United States Patent [19]

Holmqvist et al.

[11] Patent Number: 5,582,684
[45] Date of Patent: Dec. 10, 1996

[54] METHOD OF DETERMINING DEGREE OF REDUCTION IN A SULFATE LIQUOR USING IR AND UV SPECTROSCOPY

[75] Inventors: Richard Holmqvist, Bromma; Torbjörn Jönsson, Älvsjö, both of Sweden

[73] Assignee: STFI, Stockholm, Sweden

[21] Appl. No.: 256,413

[22] PCT Filed: Dec. 9, 1992

[86] PCT No.: PCT/SE92/00850

§ 371 Date: Sep. 29, 1994

§ 102(e) Date: Sep. 29, 1994

[87] PCT Pub. No.: WO93/14390

PCT Pub. Date: Jul. 22, 1993

[30] Foreign Application Priority Data

Jan. 9, 1992 [SE] Sweden ................................. 9200049

[51] Int. Cl.⁶ ..................................................... D21C 7/12
[52] U.S. Cl. ............................... 162/49; 162/61; 162/62; 162/238; 436/120; 436/123
[58] Field of Search ................................. 162/49, 61, 62, 162/82, 198, 238; 436/120, 123

[56] References Cited

U.S. PATENT DOCUMENTS

| | | | |
|---|---|---|---|
| 4,238,198 | 12/1980 | Swaim et al. ........................ 23/230 R |
| 4,733,084 | 3/1988 | Oosaka ..................................... 250/373 |
| 4,743,339 | 5/1988 | Faix et al. ................................. 162/49 |
| 4,889,593 | 12/1989 | Tikka et al. ............................... 162/49 |
| 5,282,931 | 2/1994 | LeClerc et al. ........................... 162/49 |

FOREIGN PATENT DOCUMENTS

| | | |
|---|---|---|
| 0053289 | 6/1982 | European Pat. Off. |
| 2910945 | 10/1979 | Germany. |
| 9117305 | 11/1991 | WIPO. |

Primary Examiner—Donald E. Czaja
Assistant Examiner—Dean T. Nguyen
Attorney, Agent, or Firm—Burns, Doane, Swecker & Mathis, L.L.P.

[57] ABSTRACT

The invention relates to a method of determining the concentration of sulfide and optionally also of polysulfide in liquors and solutions of smelt deriving from the sulfate process. According to the method, the concentrations are determined by measuring the light absorption of the liquor or the solution in the ultra-violet range. According to one preferred embodiment, the method is applied to determine the degree of reduction in sulfate liquor and smelt derived from burning liquor, wherein the concentrations of sulfate, thiosulfate and optionally sulfite and/or carbonate are determined by measuring the light absorption of the liquor or the solution in the infrared range, whereafter the degree of reduction is calculated from the measuring data obtained.

6 Claims, No Drawings

METHOD OF DETERMINING DEGREE OF REDUCTION IN A SULFATE LIQUOR USING IR AND UV SPECTROSCOPY

The present invention relates generally to a method of determining the sulfide concentration and optionally also the polysulfide concentration of waste liquors and smelt solutions obtained in the manufacture of sulfate pulp. The invention particularly relates to the application of this method in determining the degree of reduction in green liquor and in smelt that derives from liquor combustion processes.

When burning sulfate waste liquor in soda recovery units with the intention of recovering the liquor, one of the main objects of the process is to reduce sulfur to sulfide. The degree of reduction indicates how much of the sulfur present in the waste liquor or in the smelt exists in the form of sulfide. This constitutes an important measurement of the quality of the waste liquor, since it is the sulfide form of sulfur that is active in the pulp cooking process, whereas sulfur in any other form can be considered to be a useless ballast material.

The white liquor used in pulp cooking processes is produced by causticizing green liquor and isolating the calcium carbonate (mesa) formed. The green liquor is produced by dissolving the smelt from the furnace hearth in a weak liquor obtained when washing pulp after the cooking process. It is thus the sulfide content of the smelt which is significant to the sulfide content of the white liquor, and therewith its quality. Consequently, it is important to be able to determine the degree of reduction in the smelt and therewith to effect this determination quickly and to obtain accurate and well-reproducible measuring results.

Hitherto, samples of the green liquor are taken manually several times over a calendar day, when determining the reduction degree of the smelt. These samples are then analyzed to determine the concentrations of different sulfur-containing compounds with the aid of a number of titration processes, from which the reduction degree can then be determined. This method is complicated and slow. In recent times, automatic titration apparatus have been developed which facilitate the task of determining these concentrations.

Automatic titrating apparatus, however, are encumbered with a number of drawbacks. For instance, such apparatus are relatively slow and it is scarcely possible to increase the measuring frequency above a few times per hour. Handling of liquids is difficult to effect during the titration processes, and requires a high degree of precision. Furthermore, the requisite determination of sulfate concentrations requires the use of conditioning chemicals, which is not entirely acceptable from the aspect of health.

The aforesaid drawbacks are eliminated by the present invention. According to the invention, the concentrations of sulfide and optionally also polysulfide in liquors and solutions of smelt deriving from the sulfate process are determined by measuring the light absorption of the liquor or the solution in the ultraviolet range (UV-absorption assaying). According to one preferred embodiment of the invention, the degree of reduction in sulfate liquor is determined by measuring the liquor concentrations of sulfide, sulfate, thiosulfate and optionally sulfite and polysulfide and/or carbonate and calculating the reduction degree from the determined concentrations, wherein the concentrations of sulfate, thiosulfate and optionally sulfite and/or carbonate are determined by measuring the light absorption in the infrared range (IR-absorption assaying), and the concentration of sulfide and optionally polysulfide is/are determined by measuring the light absorption in the ultraviolet range (UV-absorption assaying).

The smelt produced in the soda recovery unit or boiler includes three forms of sulfur, namely sulfide, polysulfide and sulfate. The polysulfide concentration is normally negligible. When dissolving the smelt to form green liquor, a minor part of the sulfide is oxidized, to form primarily thiosulfate. The sulfate, on the other hand, is not affected. A minor quantity of sulfite may also be present. The degree of reduction R can now be defined in accordance with the following:

$$R = \frac{\text{The amount of sulfur present as sulfide}}{\text{Total sulfur content}}$$

The degree of oxidation Ox is defined as follows:

$$Ox = \frac{\text{The amount of sulfur present as sulfate}}{\text{Total sulfur content}}$$

The following relationship applies when using the index "m" for the smelt and "gl" for the green liquor:

$$R_m = 1 - Ox_m$$

$$Ox_m = Ox_{gl}$$

and thus $$R_m = 1 - Ox_{gl}$$

It is assumed in these equations that the polysulfide content of the smelt is negligible.

Thus, the degree of reduction in the smelt can be determined by determining the sulfate content and the total sulfur content of the green liquor. Naturally, a correction must be inserted for the quantity of sulfur which is introduced in different forms with the weak liquor used in the dissolution process.

According to the preferred embodiment of the invention, the concentrations of sulfide, sulfate, thiosulfate and optionally sulfite and optionally polysulfide are determined in a diluted liquor, from which the total sulfur content is calculated. The sulfate, thiosulfate and optionally sulfite concentrations are determined by means of IR-absorption assaying. Sulfate ions, thiosulfate ions and sulfite ions all absorb IR-light pronouncedly within the range from 1,500 to 800 $cm^{-1}$ in aqueous solution, and the assay is preferably carried out within this range. If desired, the concentration of carbonate can also be determined by IR-absorption assaying in the aforesaid range.

The IR-absorption assay is most suitably carried out as a Fourier-Transform-IR, which is a method well known in the art. The absorption peaks of the aforesaid ions overlap one another, although this problem can be overcome by using a multivariate calibration technique, e.g. PLS, in a manner known per se.

Water also has a pronounced absorption within the aforesaid spectral range of 1,500–800 $cm^{-1}$. Consequently, the path of the light beam through the liquor in the measuring cuvettes used must be very short, in the order of 10 μm. This enables the use of a known method applying attenuated total reflection (ATR), which enables very short light paths through the liquid to be obtained without the requirement of a thin liquid layer.

The sulfide content is determined by means of UV-absorption with the aid of a moderately diluted solution of green liquor, i.e. a green liquor solution which has been diluted from about once to ten times. The sulfide is present in the aqueous solution in the form of hydrosulfide ions $HS^-$, which exhibit a highly pronounced absorption between 200 and 250 nm in the UV-range. The absorption contribution from remaining components in the green liquor is either negligible within this range or may be compensated for. Thus, these contributions do not disturb the determination of the sulfide content, something which is unexpected to the skilled person. This represents an important advantage of the inventive method. However, the high absorption of the sulfide ions means that the liquor must either be very strongly diluted or that a measuring cuvette having a very small layer thickness must be used. Problems concerning the accuracy to which the assay is carried out are also created when the liquor is strongly diluted, and the risk of oxidation of the sulfide ions increases. It is therefore preferred to work with measuring cuvettes of small layer thicknesses. The difficulties resulting therefrom can be overcome by the skilled person.

The results obtained by the assays are best processed in a computer with the aid of a mathematical model which expresses the relationship between measured IR and UV spectra and the concentrations of the compounds concerned. The aforesaid special method PLS is also included in this.

In exceptional cases, the operating conditions of the soda recovery unit may be such that a percentage of the total sulfur content is present in the form of polysulfide. Such operating conditions are undesirable from the corrosion aspect. However, in accordance with a further development of the present invention, the polysulfide concentration can be determined by UV-absorption assaying in the wavelength range of 200–300 nm. Such an assay should be used primarily as a warning signal. Secondarily, the assay can be used to correct determination of the degree of reduction. According to a further development, it is also possible to determine the carbonate concentration, since this ion will also absorb pronouncedly in the aforesaid IR-range of 1,500–800 $cm^{-1}$. The result can then be presented in some suitable manner.

The present invention enables the degree of reduction of the liquor to be determined on-line, and therewith also the degree of reduction of the smelt. This is effected by taking a suitable sample from a green-liquor conduit or tank in the process. The sample taken is diluted and filtered, whereafter the sample is introduced into an FTIR-instrument and a UV-spectrophotometer either continuously or intermittently at high frequencies, e.g. in the order of several times per minute. The measuring values obtained are then processed in a computer in accordance with the aforegoing, and the result is presented in some appropriate manner, for instance on a screen or on a printout. According to a further development of the invention, the control parameters of the soda recovery unit or boiler, such as the air supply, can be influenced directly in accordance with the measurement values obtained.

The inventive method has been described in the aforegoing mainly with reference to determining the concentrations of sulfide and polysulfide and therewith the associated degree of reduction in green liquor. It will be understood, however, that the invention is not limited solely hereto and that the invention can be applied to each sulfide-containing liquor and solution that is likely to occur in the sulfate process. It is also conceivable to apply the method with suitable modifications which will enable sulfide concentrations to be determined directly from a smelt.

The present invention affords several important advantages over those methods previously applied with regards to titration-based methods for determining the degrees of reduction in liquors and smelts.

The method according to the invention is based on optical measuring or assaying processes and no intermediate steps which include chemical reactions are required. Such reactions always involve uncertainty in the course taken by the reactions and with regard to the amounts of reagent added. Furthermore, when practicing the present invention, it is not necessary to separate the liquor into different components, which is highly beneficial from a handling aspect. A further important advantage is that the measuring frequency can be increased considerably in comparison with earlier known measuring or assaying methods. This allows the quality of the recovered liquor to be monitored in a much more effective and efficient manner.

We claim:

1. A method for determining the degree of reduction in a sulfate liquor or a sulfate smelt solution, said method comprising the steps of:

(a) measuring the light absorption of the sulfate liquor or the smelt solution in the infrared range of 1500 to 800 $cm^{-1}$ to produce an IR absorption spectra;

(b) measuring the light absorption of the sulfate liquor or the smelt solution in the ultraviolet range of 200 to 250 nm to produce a UV absorption spectra, without separation of the sulfate liquor or the solution into different components;

(c) calculating the concentrations of sulfate, thiosulfate and optionally sulfite and/or carbonate in the sulfate liquor or the smelt solution from the IR absorption spectra by using a computer-implemented mathematical model in combination with a multivariate calibration technique;

(d) calculating the concentration of sulfide and optionally polysulfide in the sulfate liquor or the smelt solution from the UV absorption spectra by using a computer-implemented mathematical model in combination with a multivariate calibration technique; and (e) determining the degree of reduction of the sulfate liquor or the smelt solution from the concentration of sulfide and optionally polysulfide, and the concentrations of sulfate, thiosulfate and optionally sulfite and/or carbonate calculated in steps (c) and (d).

2. A method according to claim 1, wherein the IR-absorption is measured in an aqueous solution.

3. A method according to claim 2, wherein the IR-absorption measuring process is a Fourier-Transform-IR (FTIR).

4. A method according to claim 2, wherein the degree of reduction is determined on a diluted aqueous solution of the liquor.

5. A method according to claim 2, wherein the IR-absorption is carried out by passing a short path of light through the liquor or solution.

6. A method according to claim 1, wherein the degree of reduction is determined on a diluted aqueous solution of the liquor.

* * * * *